United States Patent [19]

Coe

[11] Patent Number: 5,483,072

[45] Date of Patent: Jan. 9, 1996

[54] AUTOMATIC POSITION CONTROL SYSTEM FOR X-RAY MACHINES

[75] Inventor: Robert P. Coe, Dix Hills, N.Y.

[73] Assignee: Bennett X-Ray Technologies, Copiague, N.Y.

[21] Appl. No.: 286,484

[22] Filed: Aug. 4, 1994

[51] Int. Cl.[6] .................................................. G01T 1/185
[52] U.S. Cl. ............................ 250/385.1; 250/370.1
[58] Field of Search ................................ 250/370.1, 374, 250/385.1, 390.12

[56] References Cited

U.S. PATENT DOCUMENTS

3,691,382  9/1972  Somer ................................ 250/370.1
4,510,391  4/1985  Goganov et al. ..................... 250/374
4,800,580  1/1989  Houtman et al. ..................... 378/75
4,843,246  6/1989  Benes et al. ....................... 250/491.1

*Primary Examiner*—Davis L. Willis
*Assistant Examiner*—Richard Hanig
*Attorney, Agent, or Firm*—Meltzer, Lippe, Goldstein et al.

[57] ABSTRACT

An x-ray machine, such as a mammography machine, comprises a source of a narrow beam of radiation which scans across an object, e.g., a breast, to be imaged. A sensor for the narrow beam moves in the same direction as the narrow beam. The sensor generates an output signal which indicates the position of the beam relative to a specific location on the sensor. A control circuit receives the signal from the sensor and outputs a control signal to regulate the position of the beam relative to the sensor.

4 Claims, 8 Drawing Sheets

ELEMENT #1

FIG. 7A
ELEMENT #1

FIG. 7B
ELEMENT #2

AUTOMATIC POSITION CONTROL SYSTEM FOR X-RAY MACHINES

FIELD OF THE INVENTION

The present invention relates to an automatic position control system for x-ray machines such as mammography machines. In particular, the present invention relates to a position control system which maintains the position of a scanning x-ray beam in coincidence with the center of an x-ray sensor that moves with the scanning x-ray beam. The present invention also relates to the x-ray sensor used in such a position control system.

BACKGROUND OF THE INVENTION

Figure 1:
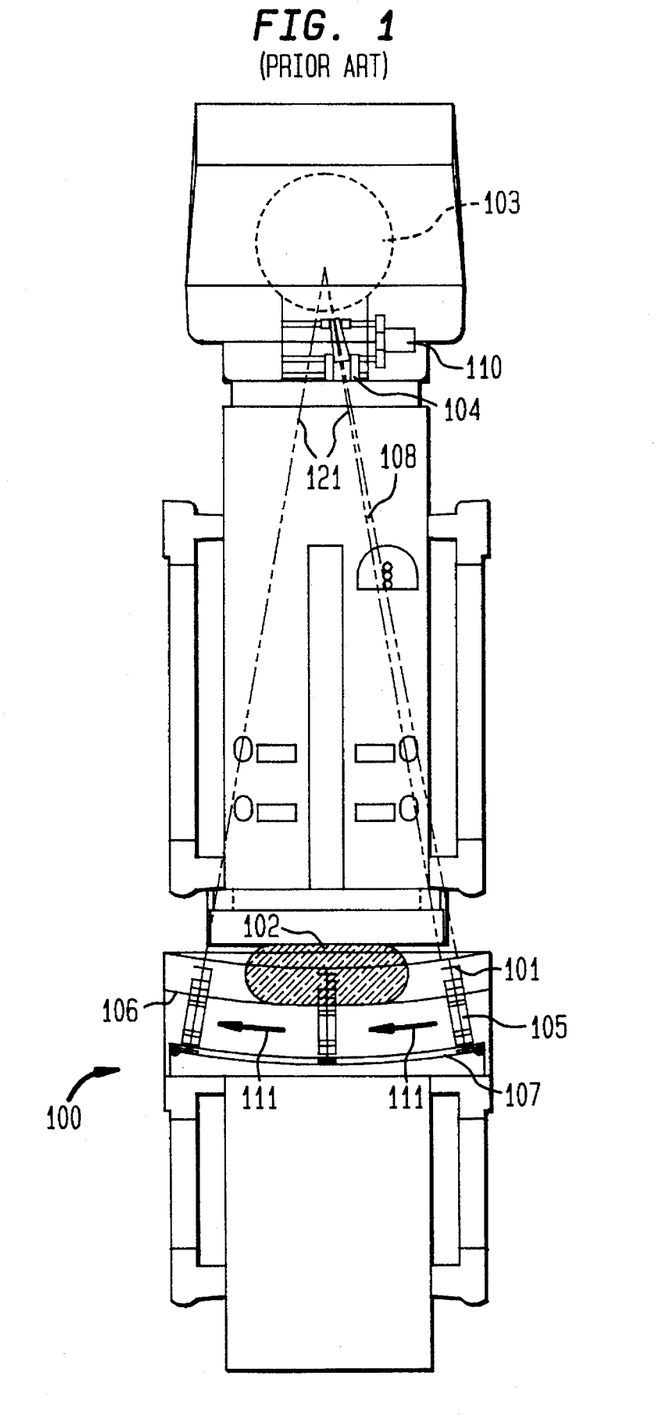
FIG. 1 is a schematic diagram illustrating a prior art mechanically sweeping slot scanning mammography machine.

FIG. 1 is a schematic diagram illustrating a prior art mammography machine (100). The mammography machine (100) has an x-ray source (103), a beam limiting device (104) and a support platform (106) for positioning a part of the patient's body, which in this case is the breast (102). The mammography machine (100) also includes the x-ray sensor (101) and the CCD detector (105). The x-ray sensor (101) is attached to the CCD detector (105) and moves along the track (107). The x-ray sensor (101) is used to determine the quantity of energy passing through the breast (102). The CCD detector (105) is used to create an image for diagnostic purposes. In other mammography machines, the CCD sensor (105) is not utilized and the image is made on a film.

The x-ray sensor (101) is also used in automatic exposure controls to control the time of exposure of an x-ray source (103) and, when film is used, to provide the proper optical density on the film. This type of sensor might include solid state devices, ionization chambers or photo-multiplier tubes.

In several applications, a narrow x-ray beam (108) is scanned across the breast (102). A slot scanning x-ray procedure is one such application. In slot scanning applications, a beam limiting device (104) is swept to produce the narrow scanning x-ray beam (108). It is desirable to know the location of the scanning x-ray beam (108) as well as its intensity.

To obtain an x-ray exposure, the beam limiting device (104), the x-ray sensor (101) and the CCD detector (105) traverse the breast (102) at a constant velocity. Thus the narrow x-ray beam (108) scans across the breast (102) from right to left as indicated by the arrow (121). During exposure of the breast (102), the CCD detector (105) and sensor (101) move along track (107) from right to left as indicated by the arrows (111).

Figure 2:
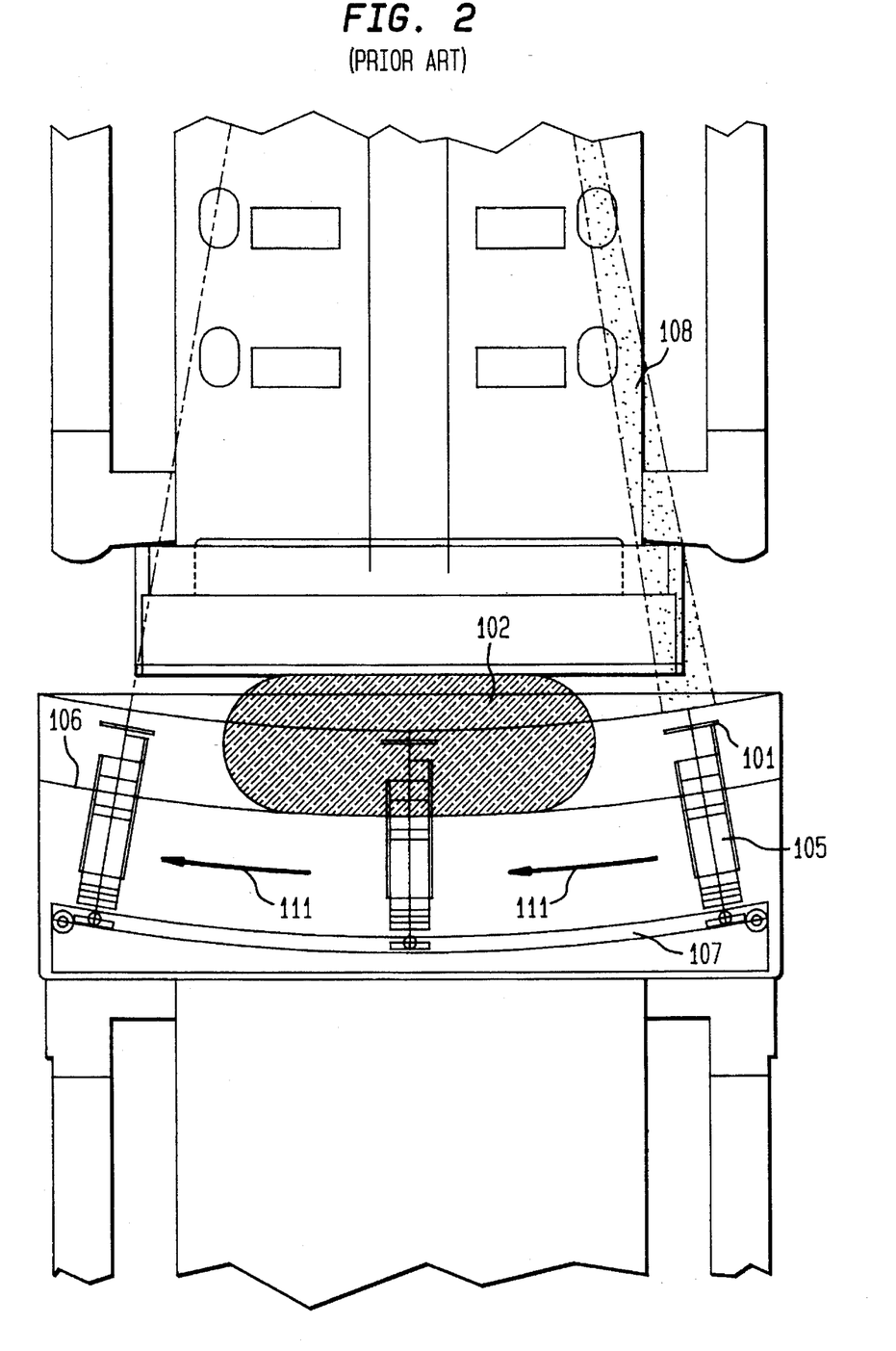
FIG. 2 is an enlargement of the lower portion of the mammography machine shown in FIG. 1, detailing the sensor, the CCD detector and the track used for movement.

FIG. 2 is an enlargement of the lower portion of the x-ray machine shown in FIG. 1, detailing the x-ray sensor (101), the CCD detector (105) and the track (107) used for movement. FIG. 2 also shows arrows (111) which indicate the direction of movement along the track (107).

Figure 3:
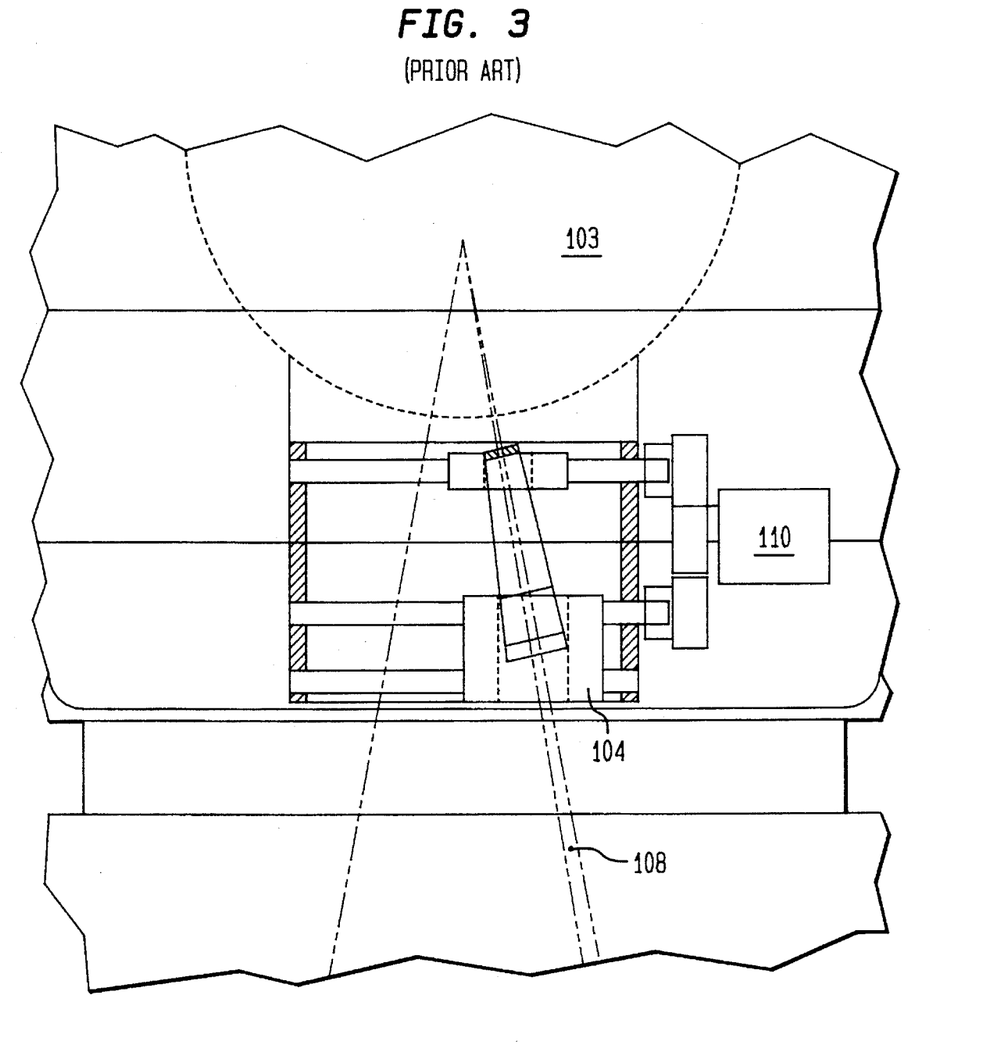
FIG. 3 is an enlargement of the upper portion of the mammography machine shown in FIG. 1, detailing the servo positioning motor and the beam limiting device.

The movement of the sensor (101) and detector (105) along track (107) is aligned with the scanning narrow x-ray beam (108). The x-ray beam (108) is scanned by a servo-positioning motor (110) which moves the beam limiting device (104). FIG. 3 is an enlargement of the upper portion of the x-ray machine shown in FIG. 1, detailing the servo-positioning motor (110) and the beam limiting device (104).

Slot scanning applications described in the current literature all rely on mechanical interfaces for moving the scanning x-ray beam (108), sensor (101) and the detector (105). These interfaces are complex and costly and are prone to alignment problems which reduce the quality of the produced image.

In short, the quality of a slot scanning system is a function of the location of the scanning x-ray beam (108) as well as its intensity. It is a function of the accuracy of synchronously moving the beam limiting device (104), the sensor (101) and the detector (105) in the same direction (111) across the breast (102).

In view of the foregoing, it is an object of the invention to provide an automatic position control system for an x-ray machine such as a mammography machine in which the x-ray beam and x-ray sensor synchronously scan across the breast or other part of the patient's body.

It is a principal object of the invention to provide an x-ray machine especially for mammography which includes an automatic position control system for maintaining the position of an x-ray beam with respect to an x-ray sensor without cumbersome mechanical interfaces.

It is also an object of the invention to provide an x-ray sensor for use in such a position control system, which sensor outputs a signal indicative of the position of a narrow x-ray beam.

SUMMARY OF THE INVENTION

This and other objects are achieved by the present invention which provides an automatic position control system for x-ray machines for use in mammography or other applications. The control system maintains alignment of a scanning narrow x-ray beam with a sensor. The present invention provides a servo-driven motion control system which automatically aligns the x-ray beam with the x-ray sensor.

According to one embodiment of the invention, a narrow x-ray beam is produced. The narrow x-ray beam illuminates the breast (or other body part) of the patient. The x-ray beam, after passing through the breast, is sensed by an x-ray sensor. The narrow x-ray beam and sensor move synchronously to scan across the breast. The x-ray beam is scanned by a servo-positioning motor which controls the position of a beam limiting device. The sensor is moved by a sensor positioning motor. The feedback system operates as follows: The sensor senses the position of the narrow x-ray beam relative to the sensor and sends a signal representing the x-ray beam position to a feedback amplifier. The feedback amplifier compares the signal representing the position of the x-ray beam with a preset reference signal and sends the difference (i.e., error signal) to a servo-positioning motor controller. This motor controller controls the servo-positioning motor which moves the beam limiting device to center the narrow x-ray beam over the sensor.

The sensor can be implemented by various technologies, including but not limited to an ionization chamber, a photodiode array, a CCD array or a photocell with phosphor. Illustratively, the sensor receiving the x-ray radiation is an ionization chamber which generates an ionization current. Such an ionization chamber comprises two elements (i.e., electrodes) separated by a gas or air. One of the element comprises a plurality of sensing strips separated by resistors. Furthermore, this element has two terminals each terminated by a terminating resistor. The voltage between the two terminals is a signal representing the position of the x-ray beam.

According to another embodiment of the x-ray sensor, a plurality of photodiodes are connected in series and separated by resistors. The sensor has two terminals (at either end of the series connected photodiodes), with each terminal being terminated by a resistor. The voltage between the two terminals is a signal which represents the position of the x-ray beam.

The present invention solves the problem of simultaneously correlating and achieving the correct alignment of the sensor and the beam limiting device without cumbersome mechanical interfaces. The x-ray positioning sensor of the present invention allows for an automatic alignment through its ability to sense the position of the scanning narrow x-ray beam. The mechanical mechanisms used in the prior art to move the sensor are replaced by a simple servo-driven motion control system.

DETAILED DESCRIPTION OF THE INVENTION

Figure 4:
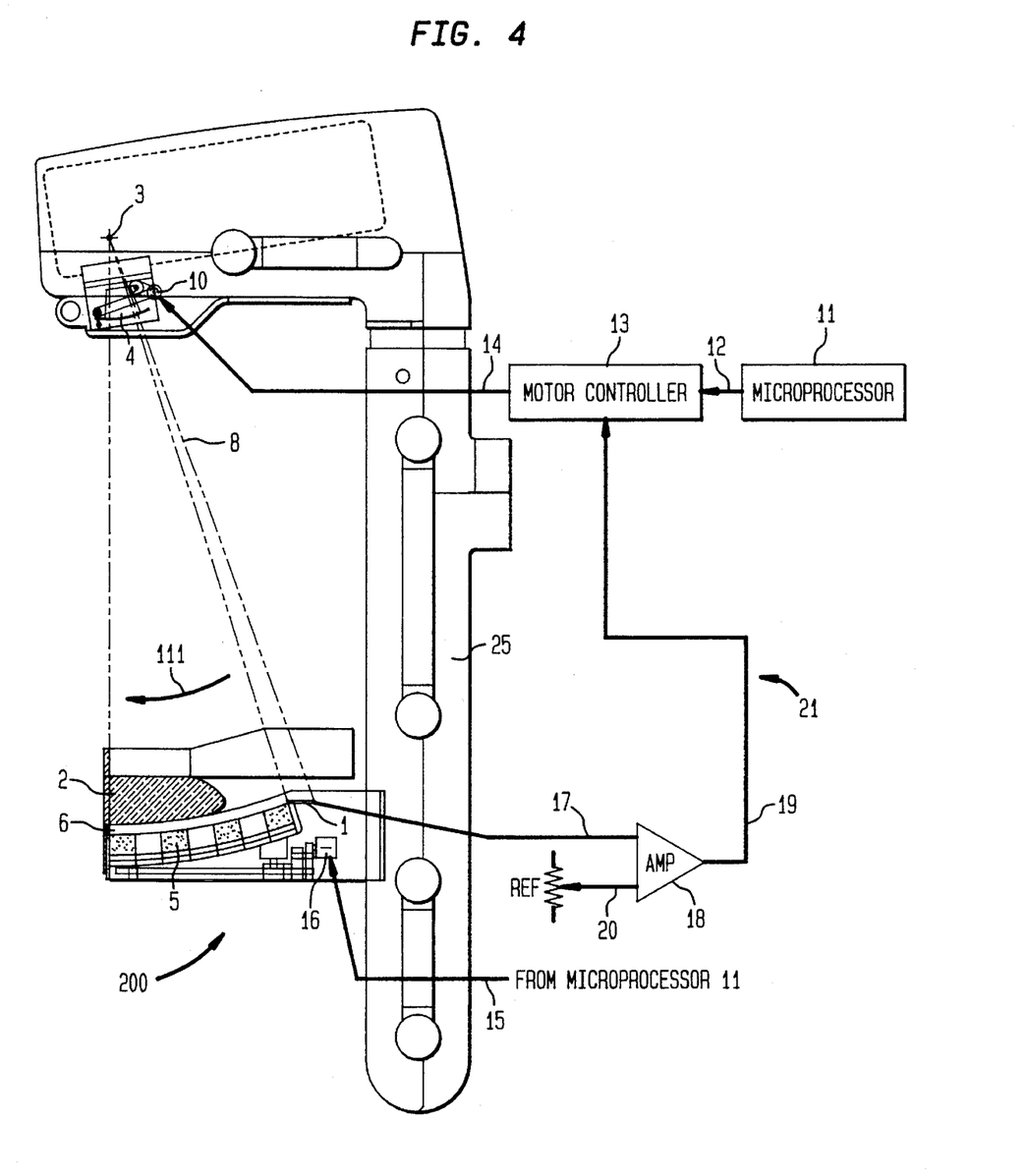
FIG. 4 is a schematic diagram of the present invention, illustrating the automatic position control system for a mammography machine.
Figure 5:
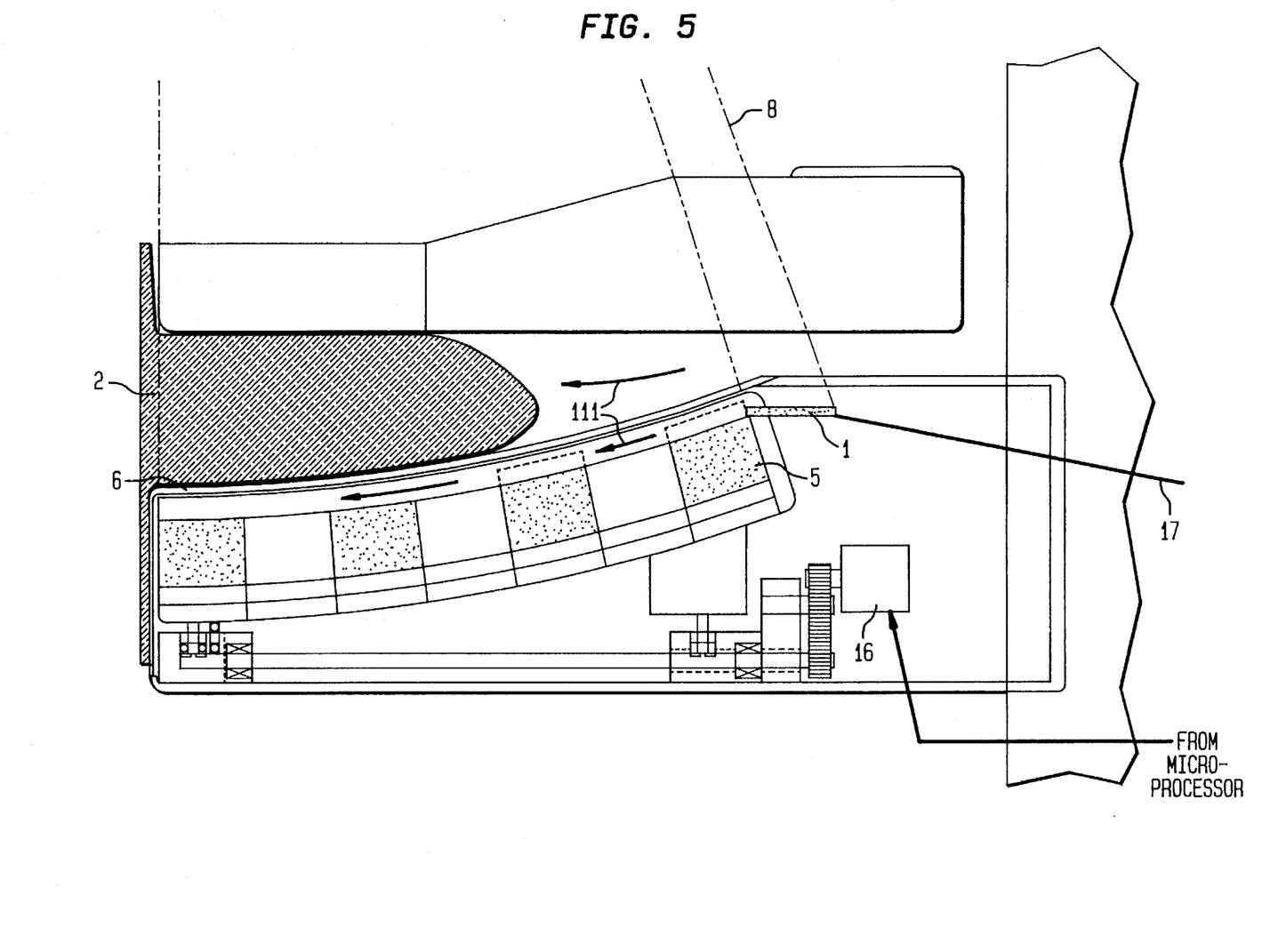
FIG. 5 is an enlargement of the lower portion of the embodiment of the present invention shown in FIG. 4, detailing the sensor positioning motor used for movement.
Figure 6:
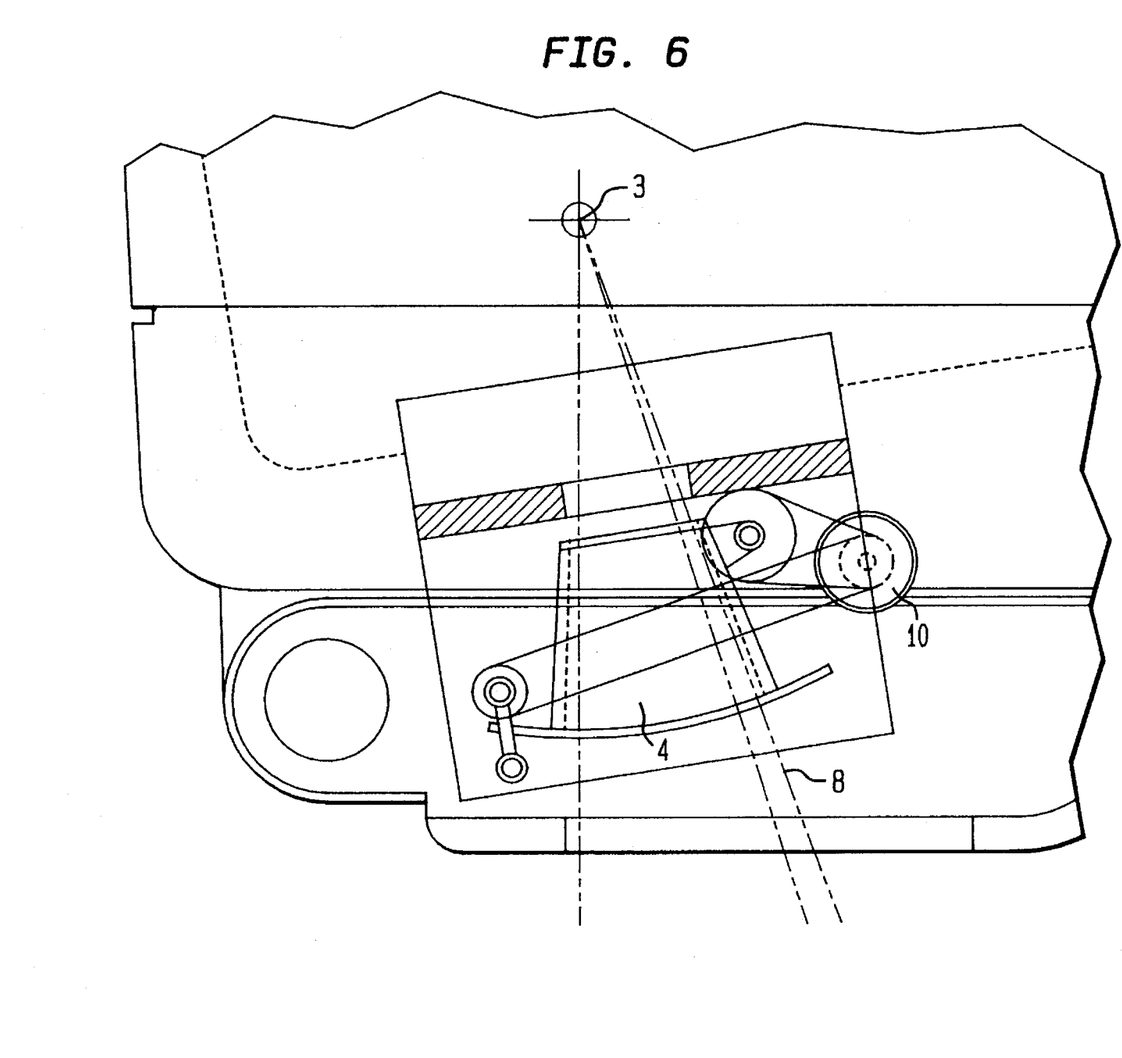
FIG. 6 is an enlargement of the upper portion of the embodiment of the present invention shown in FIG. 4, detailing the servo positioning motor and the beam limiting device.

A mammography machine (200) in accordance with an illustrative embodiment of the present invention is shown in FIG. 4. The system (200) has an x-ray source (3) and an x-ray sensor (1) which is associated with a support platform (6). The support platform (6) supports an object to be examined, e.g., a patient's breast (2). The foregoing elements are all attached to a column (25). The mammography system (200) also includes a CCD detector (5) for forming an image of the x-rayed breast. Alternatively, a film may be used to form the image instead of the CCD detector.

The x-ray source (3) has a beam limiting device (4) which defines a narrow beam of x-ray energy (8) covering the sensor (1). It is desirable in such a system to keep the x-ray sensor (1) centered under the x-ray beam (8) as the beam is scanned across the object (2) to be imaged. Thus, the x-ray beam (8) and sensor (1) travel synchronously in the direction indicated by the arrows (111).

The x-ray imaging system (200) has a microprocessor (11) which receives predetermined system requirements, such as a sweep time, from a system operator. Based on these inputs, the microprocessor (11) provides a first control signal (12) to a motor controller (13). In turn, the motor controller (13) provides a second control signal (14) to a servo-positioning motor (10). The servo-positioning motor (10) moves the beam limiting device (4) thus scanning the narrow x-ray beam (8). The programming and operation of the microprocessor to perform this function is well known.

The microprocessor (11) also provides third control signal (15) to a sensor positioning motor (16). The sensor positioning motor (16) moves the sensor (1) and detector (5). The sensor (1) senses the position of the x-ray beam (8) and provides a fourth control signal (17) containing position information to a feedback amplifier (18). The fourth control signal (17) is dependent on the position of the x-ray beam (8) relative to the sensor (1).

This fourth control signal (17) is part of a feedback loop (21) which controls the position of the x-ray beam (8) to keep it centered over the sensor (1). The feedback amplifier (18) compares the fourth control signal (17) to a reference signal (20) and outputs a fifth control signal (19) which represents the difference between the fourth control signal (17) and the reference signal (20). The fifth control signal (19) is input into the servo-positioning motor controller (13) and completes a feedback loop (21). The closed loop feedback (21) comprises the positioning sensor (1), the amplifier (18), the motor controller (13), and the servo-positioning motor (10). The motor controller (13) controls the servo-positioning motor (10) which in turn moves the beam limiting device (4) so that the x-ray beam (8) is centered over the sensor (1).

An x-ray exposure is taken by starting the x-ray imaging system (200) with the narrow x-ray beam (8) at one side of the breast support platform (6). The beam limiting device (4) collimates the beam (8) to expose the CCD detector (5). As the exposure begins, the beam limiting device (4) and the sensor (1) transverse the breast (2) in the direction of arrows (111) at a constant velocity. The sensor (1) and detector (5) move synchronously with the beam (8) as driven by the sensor positioning motor (16). The positioning sensor (1) is used in conjunction with a feedback loop (21) to ensure that the x-ray beam (8) is aligned with a specified location such as the center of the sensor (1).

The sensor (1) can be implemented by various technologies, including but not limited to an ionization chamber, a photodiode array, a CCD array or a photocell with phosphor.

Figure 7A:
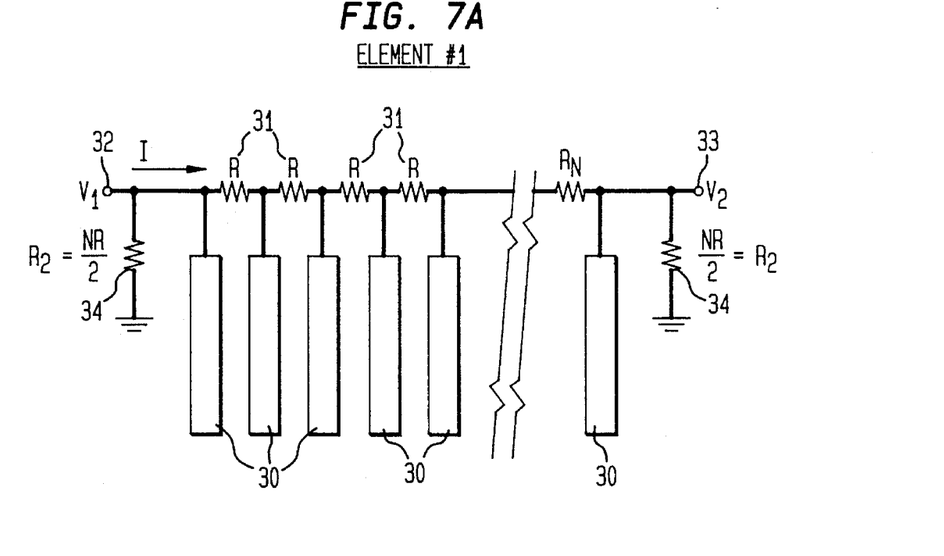
FIGS. 7(a), 7(b) and 7(c) are schematic diagrams illustrating one embodiment of the present invention, where an ionization chamber sensor is used for sensing the x-ray beam and keeping the sensor aligned to the beam.
Figure 7B:
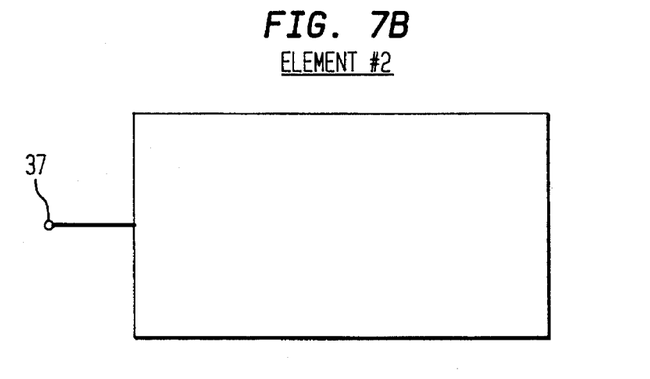
Figure 7C:
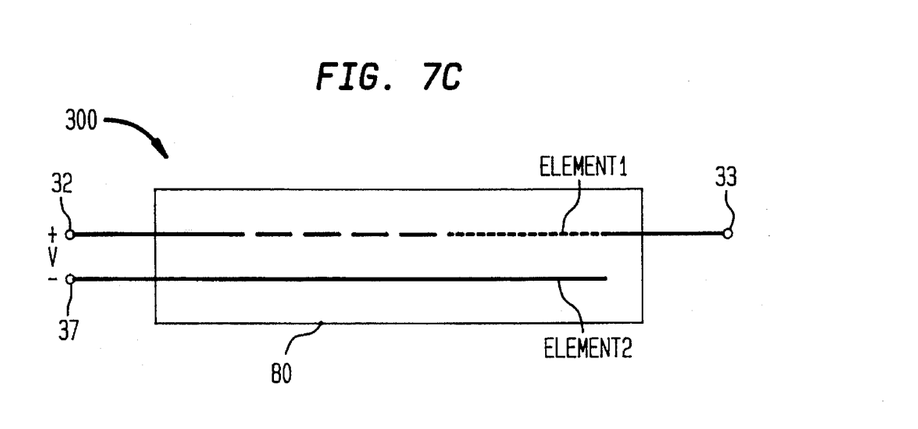

According to one embodiment of the present invention, the sensor (1) is an ionization chamber (300) shown in FIGS. 7(a), 7(b) and 7(c). The ionization chamber (300) comprises an element 1 and an element 2 located in a conductive plastic housing (80) as shown in FIG. 7(c). The housing (80) is filled with a gas and the elements 1 and 2 are spaced apart by 13 millimeters. As shown in FIG. 7(a), element 1 comprises a series of 15 sensing strips (30) separated by resistors (31) of R ohms. The sensing strips are made of copper and have dimensions of 4 mm×25 mm. There are N resistors (31) of R ohms. Element 1 has two output terminals (32) and (33), each terminated by a terminating resistor (34) of $R_2$ ohms. Resistor (34) is defined by equation (1)

$$R_2 = \frac{N \times R}{2} \tag{1}$$

For example, R is 100,000 ohms and $R_2$ is 700,000 ohms. There are 15 strips and N=14 series resistors. The element 2 of FIG. 7(*b*) is made of aluminum and has dimensions of 35 mm×75 mm×0.1 mm thick.

One of the fundamental properties of x-rays is that they can ionize gases; that is, remove electrons from atoms to form ions, which can be used for measuring and controlling exposure. Gas-filled detectors, regardless of the shape or size, generally use ionization of the gas by the incoming radiation to produce a signal with a corresponding current and voltage. The important characteristic is that the current is directly proportional to or otherwise represents the intensity of the incoming radiation. The invention uses this principle to generate current in the resistors (31) and (34) and produce a voltage which indicates position as well as intensity.

When an x-ray photon ionizes the air or gas separating two sensing strips (30), free electrons are generated. A bias voltage for example 300 volts, is applied between terminal 32 of element 1 and terminal 37 of element 2 so that these free electrons generate a current I. The current I flows through the resistors (31) and generates voltages $V_1$ and $V_2$ at each output terminal (32) and (33) of element 1 respectively.

The voltage levels $V_1$ and $V_2$ are proportional to the number of resistors transversed by the ionization current I. For example, if the x-ray energy was all impinging on the left sensing strip, then the voltage at the left output terminal (32) would be $$V_1 = \frac{3 \times N \times R \times}{8} I \tag{2}$$

where I is the ionization current.

The voltage at the right output terminal (33) would be $$V_2 = V/3 \tag{3}$$

The voltages $V_1$ and $V_2$ go to a differential amplifier circuit (not shown) whose output is the difference between the two voltages. This difference voltage is given by equation (4).

$$V_1 - V_2 \tfrac{2}{3} V \tag{4}$$

The difference voltage $V_1 - V_2$ is proportional to the position of the x-ray energy. When the x-ray beam (8) is centered on the ionization chamber (300), the voltage out of the differential amplifier will be 0 volts. If the beam is off-center to the left or to the right, the voltage out of the differential amplifier will be positive or negative, corresponding to the distance from the center of the chamber (300). It can, therefore, be used in a control feedback loop (21) shown in FIG. 4, to keep the x-ray beam (8) centered over the detector (5).

Figure 8:
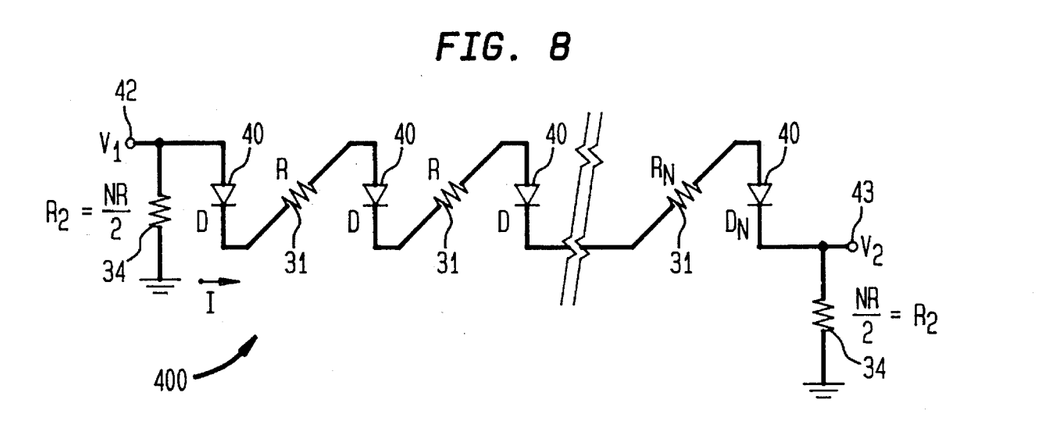
FIG. 8 is a schematic diagram illustrating another embodiment of the present invention, where a photodiode sensor is used for sensing the x-ray beam and keeping the sensor aligned to the beam.

According to another embodiment of the present invention, the sensor (1) is a photodiode (400) shown in FIG. 8. The photodiode (400) is similar to the ionization chamber, but instead of using the ionization of gas, the x-ray photons impinge on junction diodes. The photodiode (400) comprises junction diodes (40), series resistors (31) of R ohms and terminating resistors (34) of $R_2$ ohms. The value $R_2$ of the terminating resistors (34) is given by equation (1). These junction diodes (40) generate a current I proportional to the x-ray energy. This current I through the series resistors (31) generates the voltages $V_1$ and $V_2$ at the output terminals (42) and (43). The difference between the voltage represents the position of the x-ray beam (8) as described above in the ionization chamber implementation. As in the ionization chamber implementation, voltages $V_1$ and $V_2$ are used in a control feedback loop (21) shown in FIG. 4, to keep the x-ray beam (8) aligned to the detector (5).

Finally, the above described embodiments of the invention are intended to be illustrative only. Numerous alternative embodiments and equivalent structures may be devised by those skilled in the art without departing from the spirit and scope of the following claims.

I claim:

1. An x-ray sensor comprising an ionization chamber a first element separated by a gas from a second element mounted inside said ionization chamber, said first element comprising a plurality of sensing strips separated by resistors, and a first and a second terminal each terminated by a terminating resistor, wherein an output voltage obtained between said first and second terminals represents the position of an incident narrow x-ray beam.

2. The x-ray sensor of claim 1, wherein said plurality of sensing strips are arranged in a row.

3. An x-ray sensor comprising a plurality of photodiodes connected in series separated by resistors, and a first and a second terminal each terminated by a terminating resistor, wherein an output voltage obtained between said first and second terminals represent the position of an incident narrow x-ray beam.

4. The x-ray sensor of claim 3, wherein said plurality of photodiodes are arranged in a row.

\* \* \* \* \*